United States Patent [19]

Subramaniam et al.

[11] Patent Number: 4,853,232

[45] Date of Patent: Aug. 1, 1989

[54] NON-BITTER ENZYME MODIFIED CHEESE FLAVORING MATERIAL AND SPRAY DRIED PRODUCT

[75] Inventors: Anandaraman Subramaniam, Syracuse; Robert M. Ozogar, Mattydale; Carlton K. Bergsbaken, Syracuse, all of N.Y.

[73] Assignee: Borden, Inc., Columbus, Ohio

[21] Appl. No.: 43,317

[22] Filed: Apr. 28, 1987

[51] Int. Cl.[4] .................. A23C 9/12; A23C 19/086
[52] U.S. Cl. ........................ 426/35; 426/36; 426/42; 426/61; 426/63; 426/582
[58] Field of Search ............... 426/38, 33, 34, 35, 426/36, 37, 38, 42, 56, 63, 61, 43, 582

[56] References Cited

U.S. PATENT DOCUMENTS

| | | |
|---|---|---|
| 3,212,905 | 10/1965 | Arima . |
| 3,275,453 | 9/1966 | Sardinas . |
| 3,549,390 | 12/1970 | Charles . |
| 3,765,905 | 10/1973 | Kasik et al. . |
| 3,780,182 | 12/1973 | Johnson et al. . |
| 3,973,042 | 8/1976 | Kosikowski et al. . |
| 3,975,544 | 8/1976 | Kosikowski . |
| 4,172,900 | 10/1979 | Dooley . |
| 4,194,011 | 3/1980 | Invernizzi et al. . |
| 4,595,594 | 6/1986 | Lee et al. . |

OTHER PUBLICATIONS

Federal Register, vol. 34, No. 106–Wednesday, Jun. 4, 1969, Part 19.
Webb et al., "Fundamentals of Dairy Chemistry", pp. 73–75, 78–81, 662–663, 674, 693–694, Second Edition, the Avi Publishing Company, Inc., Westport, Conn.

Primary Examiner—Marianne Cintins
Attorney, Agent, or Firm—Dennis H. Rainear; Kenneth P. Van Wyck

[57] ABSTRACT

A non-bitter enzyme modified cheese flavoring composition made by effecting proteolysis in warmed hard cheese with high levels of a purified microbial coagulase enzyme. In the paste form, this composition has a high solids content and is spreadable at refrigerator temperature. In another embodiment, the composition is spray-dried as a granular product having instant cold water dispersibility.

5 Claims, No Drawings

NON-BITTER ENZYME MODIFIED CHEESE FLAVORING MATERIAL AND SPRAY DRIED PRODUCT

This invention relates to the use of a coagulase enzyme at high levels to effect proteolysis in cheese in order to produce a natural cheese flavoring material without bitterness. The natural cheese flavoring material of this invention has a smooth spreadable texture at refrigerator temperatures. In one embodiment, the cheese flavoring material is spray dried to form a granular product with instant cold water dispersibility.

BACKGROUND

Cheese is widely used by the consumer in many forms. For example, cheese itself is consumed as an end product, but also cheese or cheese flavoring material may be in a dried form or contained in salad dressings, dips, sauces and the like. Due to the wide consumer acceptance of cheese flavoring materials, there is a great demand for such products.

It is known to make a cheese flavoring material by digesting a medium only a portion of which is natural cheese. In U.S. Pat. No. 3,789,182, a powdered cheese flavoring material is provided by treating a cheese and fat blend with an esterase; combining the enzyme treated blend with a protein material (whey, buttermilk, skim milk, soy protein and the like) and drying the combined material. In U.S. Pat. No. 3,765,905, a medium containing protein, carbohydrate and natural cheese is fermented with certain organisms. The product of the fermentation may be spray dried. In U.S. Pat. No. 4,595,594, in a preliminary step a medium composed of young cheese is partially digested by lipase and a neutral protease; cream is added; and the medium which is now a blend of cheese, enzymes and cream is fermented to a product having an intensified cheese flavor.

The present invention relates to use of a coagulase enzyme at very high levels to effect proteolysis in cheese. Until recently, the calf gastric enzyme, rennin, was used almost exclusively to clot or coagulate milk as the first step in commercial cheese making. However, during the decade 1962-1972 there developed a shortage of calf stomachs and cheese makers resorted to rennet substitutes. There are now on the market safe and suitable milk-clotting (coagulase) enzymes. Rennet and the other coagulases now on the market clot fresh milk at a pH 6.2-6.8. At these pH levels, the proteolytic activity of coagulase is extremely low. Coagulase can contribute to the proteolysis of cheese during curing because of the lower pH of cheese. However, cheesemakers have generally limited the amount of coagulase used to only the amount needed to coagulate the milk because of the adverse effects of high levels of coagulase on cheese quality and flavor. When cheese curd or cheese is fermented with only a protease enzyme source, it has been the experience of cheesemakers that the product is bitter. Such experience is disclosed in U.S. Pat. No. 4,595,594. In that patent, it was reported that when cheese curd or cheese was fermented with only a neutral protease as an enzyme source, the product was bitter.

Surprisingly, it has now been found that it is possible to make a non-bitter cheese product by the fermentation of cheese with certain proteases.

SUMMARY OF THE INVENTION

The invention includes both products and process.

The product of this invention in one embodiment is cheese flavoring material in paste form that can be eaten as is or that may be added to foodstuff to impart a cheese flavor to the foodstuff. The material is a proteolyzed mixture of hard cheese and high levels of a purified microbial coagulase. Surprisingly the product is non-bitter. The product is also characterized by its high solids content (60-65%) and a smooth, spreadable texture at refrigerator temperatures (40°-45° F.).

In a second embodiment, the cheese flavoring material is a spray dried product made by spray drying the proteolyzed mixture of hard cheese and a high level of a purified microbial coagulase. The spray dried product can be used as a condiment with foods. For instance, it may be sprinkled in spaghetti, pizza and the like. It can be used in cooking and baking to make products with a cheese flavor. Since it disperses easily in cold water, it is especially useful to flavor sauces and the like.

The process of this invention comprises incubating a mixture of softened hard cheese and high levels of a purified microbial coagulase until the mixture thins; inactivating the coagulase; and homogenizing. The homogenate has a high solids content (60-65%). The process of this invention in one embodiment includes the spray drying of the high solids homogenate. The process of spray drying at high solids as compared with a process of spray drying at low solids results in two important advantages to the spray dried product.

These advantages are: (1) improved flavor retention, and (2) a granular product with instant cold water dispersibility. With certain varieties of cheeses such as six month aged cheddar, the process of this invention eliminates the need to use an emulsifying salt in producing a cheese flavor paste.

DETAILED DESCRIPTION OF THE INVENTION

The present invention is directed to preparing a "non-bitter" enzyme-modified cheese flavoring material by the digestion of warmed cheese with certain protease enzymes. The cheese should be a cheese that is at least 6 months old. The cheese is shredded and heated to 105° F.-110° F. in a double action swept surface kettle. A purified microbial coagulase is added to the softened cheese (0.5-1% by weight of the cheese). The mixture is incubated at 105°-110° F. for 2 to 3 hours depending upon the type of cheese employed. When the mixture has thinned, it is heated to 170° F. and held for approximately 10 minutes for inactivation. Prior to heating to inactivate, an emulsifying salt such as sodium hexametaphosphate (about 2% on solids basis) is added for the stability of the emulsion and to prevent "oiling off" when young cheese is employed and/or when the slurry is to be spray dried. If the cheese flavor is to be used as a paste the inactivated cheese slurry is homogenized, cooled, packaged and stored at refrigerator temperatures.

If the cheese flavoring material is to be used as a spray dried product, the inactivated cheese slurry (58% solids or higher) is homogenized and spray dried. In the examples of this invention the slurry was homogenized at 1000 psi and spray dried at feed pressures varying from 2000 to 5000 psi. The inlet and outlet temperatures of the spray dryer were maintained at 400±20° F. and 190±10° F., respectively.

In order to increase the final solids content of the product, an appropriate amount of a carrier such as hydrolyzed cereal solids may be added to the slurry prior to homogenization. The amount of a carrier added is such that the feed to the dryer will have up to 80% solids content. The spray drying conditions will be similar to those mentioned above.

If a lipolyzed flavor note is desired in the product, a lipase may be added (up to about 1.5% by weight of cheese) at the same time as the coagulase.

The cheese of this invention is a suitably ripened natural cheese. Generally, the cheese should be at least 6 months old although the minimum age depends on the type of cheese used. If the cheese is too young, it will not soften at the preferred digestion temperatures (105°-110° F.). The cheese of this invention may be any natural ripened hard cheese such as Cheddar cheese, Colby cheese, Parmesan cheese, Swiss cheese, Muenster cheese, Gouda cheese and mixtures thereof. These cheeses have a solids content of at least 60%. Cheeses that have at least 60% solids content are called hard cheeses.

The preferred coagulase for use in this invention is purified microbial coagulase. Rennet is the coagulase enzyme that is generally used in making cheese from milk. Commercial rennet preparations are standardized in activity so that one pound is used to coagulate 5000 lbs. of milk, which contains about 600 lbs. of milk solids. This proportion corresponds to about 0.167% of the standardized commercial rennet preparation based on milk solids. Assuming a cheese (such as cheddar) with 60% solids, this amount of rennet translates to 0.100% rennet based on the weight of the cheese.

The clotting strengths of other commercially available coagulase preparations are compared to the standardized rennet preparation as the standard. For instance, one pound of a triple strength coagulase would coagulate three times as much milk as one pound of rennet. In the preferred process of this invention, a triple strength coagulase is used in an amount equal to about 0.5%-1% by weight of hard cheese or 0.83% to 1.67% by weight of hard cheese solids. If one were to compare cheese solids in the process of the present invention with milk solids used in the cheese making process, then the weight amount of a single strength coagulase used for proteolysis of the cheese in the present invention would be 15 to 30 times the amount of the standardized rennet preparation that would be used in the cheese making process to coagulate a weight of milk solids corresponding to the weight of cheese solids to be proteolyzed by the coagulase.

It is contemplated that any purified microbial coagulase, that is suitable for use as a coagulase in the cheesemaking process, can be used as the enzyme of this invention. Commercially available coagulases that have been used in this invention include "Liquid Sure-Curd", a standardized triple strength solution of fermentation derived milk-clotting enzyme elaborated by *Endothia parasitica*, a product of the Pfizer Corporation; "Renzyme", a standardized double strength solution of fermentation derived milk-clotting enzyme elaborated by *Mucor pusillus* variant Lindt, a product of Marshall Products, a division of Miles Laboratory; and "New Marzyme" a standardized single strength solution of fermentation derived milk-clotting enzyme elaborated by *Mucor miehei*, a product of Marshall Products, a division of Miles Laboratory.

The use of lipase in the process and product of this invention is entirely optional. It was used in the examples because lipolyzed flavor notes were desired. The amount that is used, if any, is determined by how strong a flavor is desired. In the examples, the lipase "Italase" Lipase C, a product of Dairyland Food Laboratories, Inc. as described in their Technical Bulletin GEB No. 2, was used in an amount of about 1.5% by weight of cheese. Other commercial lipases might be used in amounts that have equivalent lipase activity.

For the stability of the emulsion of this invention when young cheese is used or when the emulsion is to be spray dried, emulsifying salts are added to the emulsion in an amount up to about 2% on a solids basis. The emulsifying salt of preference is sodium hexametaphosphate.

In one embodiment of the spray dried product of this invention hydrolyzed cereal solids are added as a carrier to the cheese slurry before the enzymes are inactivated. It is contemplated that other carriers may be used such as whey solids, buttermilk solids and skim milk solids. One preferred carrier is 10 D.E. hydrolyzed cereal solids which are obtained from the Grain Processing Corporation.

In the process of this invention, cheese is shredded in a food processor or otherwise cut into very small pieces. The shredded cheese is then warmed in any suitable container that provides mixing means. The equipment of choice is a double action swept surface kettle. The cheese is preferably warmed to 105° F.-110° F., although the temperature of the softened cheese may be as low as 80° F. or as high as 120° F. A small amount of water is added to the cheese to help heat transfer until the cheese warms. Coagulase is added to the warmed cheese. The triple-strength coagulase, "Liquid Sure-Curd", is the preferred coagulase. It is added to the warmed cheese in an amount of 0.5-1% based on the weight of cheese. The amount of coagulase added is very high when compared with the amount added to milk for normal coagulation.

The lipase "Italase" or any comparable product, may also be added, if desired, up to about 1.5% by weight of the cheese, for the enhancement of the cheese flavor that is developed in the product, with fatty acid (lipolyzed) flavors. The lipase may be purchased in dry form and if dry, is wetted with a few grams of water before being added to the cheese.

If the product is to be spray dried or if a young cheese is used, up to about 2% on a solids basis of sodium hexametaphosphate is also added. The cheese-enzyme mixture is then incubated at 105° F.-110° F. until the mixture thins. This will occur in about two hours with six-month old cheddar cheese. When thinning occurs, the slurry is heated to inactivate the enzymes. Typically, the slurry is heated to 150° C. and held for 10 minutes. If the product is to be used as a paste, the slurry is homogenized, cooled, packaged and stored at refrigerator temperatures. If the product is to be used as a spray dry product, the slurry (which has a solids content of 58% or higher) is homogenized and spray dried.

In one embodiment of the spray dried product of this invention, hydrolyzed cereal solids are added to the slurry to increase the solids content of the slurry to as high as 80%.

It is known that low solids slurries spray to a powder. The slurry of this invention because of its high solids content (at least 58%) spray dries to a granular form. The granules disperse instantly when added to cold water. The fact that granules of the product of this invention disperse instantly but powders of similar material do not disperse well may be better understood by considering the following. The granule is by definition a large unit when compared to particles of the powder. When added to a body of water, the granule will fall through the surface of the water and be readily dispersed into the water. On the other hand, each particle of the powder tends to float, and clumping may occur before the particles fall into the water. For example, when dried milk was first developed, it was sold as a powder. Unless one was very careful, a lumpy mixture was formed when one reconstituted milk powder with water. Today, dried milk is sold in granular form and the milk disperses easily when mixed with water.

If it is desirable to color the product, the color is preferably added to the slurry just prior to inactivation of the enzymes.

The process of this invention is characterized by the use of an enzyme system to modify hard cheese and reduce its viscosity without inducing any bitterness. The process of this invention uses purified microbial milk clotting enzymes (coagulases) at a pH of 4.5–4.9 so that the enzymes act as proteases. The pH of 4.5–4.9 is the optimum pH for protease activity. In contrast, coagulases are conventionally used at a pH of 6.2–6.7 for milk clotting in cheese manufacture.

The invention will be further illustrated by the examples which follow.

Example 1, 2 and 3 are based on a typical formulation and processing conditions of a successful pilot plant scale run as described below:

| (a) Formula | Weight | % Solids by Weight, Dry Basis |
| --- | --- | --- |
| Cheddar Cheese | 19.9 lbs | 95.896 |
| Liquid Sure Curd (a coagulase) | 45.4 g | — |
| Italace C (lipase preparation in solid form) | 136.2 g | 2.215 |
| Water | 100.0 g | |
| Sodium Hexametaphosphate | 90.8 g | 1.554 |
| Yellow #5 | 11.6 g | 0.202 |
| Yellow #6 | 7.8 g | 0.132 |
| (b) Processing Conditions | | |
| Feed Temperature to the Homogenizer | 140° F. | |
| Homogenization Pressure | 1000 psi | |
| Feed Pressure to the Spray Drier | 2000 psi | |
| Nozzle-Spraying System | 68/216 | |
| Inlet Temperature to the Spray Drier | 400° F. | |
| Outlet Temperature of the Spray Drier | 180° F. | |

EXAMPLE 1

Cheese Flavoring Paste 19.9 pounds of 12 month old cheddar cheese was shredded, placed in a double action swept surface kettle and warmed to a temperature of 105° F.–110° F. (A small amount of water was added to the kettle to help with heat transfer at the beginning of the warming step.) 45.4 grams of the coagulase Liquid Sure-Curd was blended into the warm cheese. 136.2 grams of the lipase Italace C in powdered form was wetted with a few grams of water and also blended into the warm cheese.

The temperature of the cheese mix was maintained at 105° F.–110° F. for about two hours, at which time the cheese thinned to a slurry. 11.6 grams of yellow #5 and 7.8 grams of yellow #6 were blended to the slurry. The slurry was then heated to about 170° F. and kept at about that temperature for ten minutes in order to inactivate the enzymes. The slurry was then homogenized at 1000 psi in a first stage of a two stage homogenizer. The homogenized product was then cooled to 110° F., packaged in plastic containers and refrigerated.

The cheese flavoring paste can be used at refrigerator temperatures as a spread for crackers, bread and the like. It can also be used for cooking and baking. For instance, it may be blended into sauces to impart a cheese flavor to the sauce.

EXAMPLE 2

Dry Cheese Flavoring Material

In this example, the cheese flavoring material was made as in Example 1 up to the point where the cheese thinned to a slurry. At this point 90.8 grams of sodium hexametaphosphate, 11.6 grams of yellow #4, and 7.8 grams of yellow #6 were blended into the cheese slurry. The slurry was then heated to 170° F. and kept at that temperature long enough to inactivate the enzymes. The slurry was homogenized at 1000 psi in the first stage of a two stage homogenizer and then spray dried.

The resulting granular product can be reconstituted to paste form when desired to be used as a paste. It is also useful as a dry ingredient for addition to cracker dough, for example, to make cheese-flavored crackers.

EXAMPLE 3

Dry Cheese Flavor With Added Solids

In this example, the cheese was made as in Example 2 except that 10 D.E. hydrolyzed cereal solids from the Grain Processing Corporation were added to the homogenized slurry just prior to spray drying, to increase the solids content of the slurry to up to about 80%. This produced a high solids slurry that spray dried well. The hydrolyzed cereal solids are bland in flavor, and thus act as a "carrier" for the cheese flavor without contributing their own flavor to the product.

Similar successful pilot plant scale runs were conducted using the same formula except for the choice of coagulase. In one set of runs, the coagulase used was the double strength product "Renzyme". In another set of runs, the coagulase used was single strength "New Marzyme." The products obtained had strong cheese flavors.

The cheese flavoring material and the spray dried product in all cases are non-bitter. If in paste form, the cheese flavoring materials in all cases has a smooth, spreadable texture at refrigerator temperatures. The spray dried product in each case is a granular product with instant dispersibility in cold water.

CONCLUSION

The cheese flavoring material when in paste form may be used as a spread on bread or crackers and the like, and thus eaten as is, as a spread. It may also be added to foods to impart a cheese flavor.

The spray dried product of this invention may be used as a condiment. It can be sprinkled over foods such as pizza or spaghetti or it can be added to other foods to impart a cheese flavor. It can be easily dispersed in water and added to other food in that form to impart to the food a cheese flavor.

The advantages of using the cheese flavoring material when in paste form include its spreadability at refrigerator temperatures which allow it to be used immediately as a spread. The cheese flavoring material has an excellent flavor and is non-bitter. The paste mixes easily with batters, sauces and the like. The advantages of using the spray dried product include an ease of storing the product on the shelf until it is ready to use. Its instant dispersibility allows it to be used easily in making sauces, doughs, and the like.

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

What is claimed is:

1. A non-bitter flavoring material that can be eaten as is or added to a foodstuff to impart a cheese flavor to the foodstuff, comprising
    a proteolyzed mixture of a cheese having at least 60% by weight solids and a purified microbial coagulase having proteolytic activity,
    said mixture having been thinned by proteolysis at a pH of less than 4.9 and at a temperature in the range of 80 degrees to 120 degrees Farenheit, and
    said coagulase being inactivated after said proteolysis.

2. The flavoring material of claim 1 further comprising a lipase.

3. The flavoring material of claim 1 having a smooth, spreadable texture at refrigerator temperatures.

4. A flavoring material according to claim 1, wherein the amount of said purified microbial coagulase based on the weight of said cheese is from about 0.5% to about 1.0%.

5. A spray-dried non-bitter cheese flavoring material comprising
    a proteolyzed, homogenized mixture of a cheese and a purified microbial coagulase having proteolytic activity, wherein the mixture is at least 60% by weight solids,
    said mixture having been thinned by proteolysis at a pH of less than 4.9 and at a temperature in the range of 80 degrees to 120 degrees Farenheit,
    said coagulase having been inactivated after said proteolysis, and
    said spray-dried material being in granular form and being instantly dispersible in cold water.

* * * * *